United States Patent [19]
Yianneskis et al.

[11] Patent Number: 5,975,076
[45] Date of Patent: Nov. 2, 1999

[54] DRY POWDER INHALERS

[75] Inventors: Michael Yianneskis, London; Gary Peter Martin; Christopher Marriott, both of East Sussex; Kwok-On Suen; Ka-lok Carroll Lee, both of London; David Ganderton, Exeter; Mukunda Timsina, Swansea, all of United Kingdom

[73] Assignee: King's College London, London, United Kingdom

[21] Appl. No.: 08/666,537

[22] PCT Filed: Dec. 30, 1994

[86] PCT No.: PCT/GB94/02829

§ 371 Date: Oct. 10, 1996

§ 102(e) Date: Oct. 10, 1996

[87] PCT Pub. No.: WO95/17917

PCT Pub. Date: Jul. 6, 1995

[30] Foreign Application Priority Data

Dec. 31, 1993 [GB] United Kingdom .................. 9326574

[51] Int. Cl.⁶ .................... A61M 15/00; A61M 16/00; B05D 7/14; B65D 83/06
[52] U.S. Cl. .............................. 128/203.15; 128/203.12; 128/203.19
[58] Field of Search .................. 128/203.12, 203.15, 128/203.19, 203.21, 203.23, 200.24, 200.23

[56] References Cited

U.S. PATENT DOCUMENTS

| | | | |
|---|---|---|---|
| 3,653,380 | 4/1972 | Hansen | 128/203.15 |
| 4,046,146 | 9/1977 | Rosskamp et al. | 128/203.15 |
| 4,200,099 | 4/1980 | Guenzel et al. | |
| 4,739,754 | 4/1988 | Shaner | 128/203.15 |
| 4,907,583 | 3/1990 | Wetterlin et al. | 128/203.15 |
| 5,113,855 | 5/1992 | Newhouse | |
| 5,239,993 | 8/1993 | Evans | 128/203.15 |
| 5,320,714 | 6/1994 | Brendel | 128/203.15 |
| 5,507,281 | 4/1996 | Kuhnel et al. | 128/203.15 |
| 5,582,162 | 12/1996 | Petersson | 128/203.15 |
| 5,673,685 | 10/1997 | Heide et al. | 128/203.12 |
| 5,685,294 | 11/1997 | Gupte et al. | 128/203.15 |

FOREIGN PATENT DOCUMENTS

| | | |
|---|---|---|
| 0 424 790 A2 | 5/1991 | European Pat. Off. . |
| 0 451 745 A1 | 10/1991 | European Pat. Off. . |
| 2041763 | 9/1980 | United Kingdom . |
| 2165159 | 4/1986 | United Kingdom . |
| 2242134 | 9/1991 | United Kingdom . |
| WO92/01470 | 5/1982 | WIPO . |
| WO90/13327 | 11/1990 | WIPO . |
| WO92/00771 | 1/1992 | WIPO . |
| WO92/04928 | 4/1992 | WIPO . |
| WO92/10229 | 6/1992 | WIPO . |
| WO92/18188 | 10/1992 | WIPO . |

*Primary Examiner*—John G. Weiss
*Assistant Examiner*—Joseph F. Weiss, Jr.

[57] ABSTRACT

A dry powder inhaler is provided which comprises a reservoir of medicament powder, a dispensing chamber for receiving a charge of powder to be dispensed having a floor upon which the powder charge lies prior to inhalation, an inlet passage having at its outlet end a nozzle protruding into the dispensing chamber directed toward the floor thereof and an inhalation passage exiting from the chamber through which the powder may be inhaled entrained in air drawn into the inhaler through the air inlet passage. The inhalation passage has an inlet at the dispensing chamber and an outlet through which the powder may be inhaled and comprises a first upstream portion having a roof and a floor both of which rise progressively with respect to a straight line drawn form the center of the inlet to the center of the outlet ad a second portion having a roof and a floor both of which fall progressively with respect to the line in the downstream direction.

15 Claims, 7 Drawing Sheets

DRY POWDER INHALERS

The present invention relates to inhalers for use in inhaling medicaments in the form of a dry powder.

Numerous inhaler designs have been devised, some for the inhalation of medicaments dispensed as an aerosol spray and others for use in inhaling medicaments dispensed as a dry powder. Dry powder inhaler designs may either be for inhaling a single dose of medicament which is placed by the user into the inhaler on each occasion of its use or else they may incorporate a multidose dispensing mechanism having a reservoir from which a single dose is dispensed within the inhaler or a series of unit doses separately held on a carrier such as a tape or disc.

In either type of dry powder inhaler, the dose is placed between the inlet and the outlet of an air passage through which the user inhales through the mouth and the dry powder is entrained into the resulting air-flow to be conducted into the lungs of the user. The medicament may either be dispensed directly as particles of medicament, optionally in the presence of an inert diluent, or else the particles of medicament may be held on the surface of larger diluent particles from which the medicament particles must be shaken loose as the medicament is entrained into the air-flow.

Difficulties arise in producing a sufficiently vigorous flow of air and a sufficiently turbulent flow of air properly to entrain the medicament and to carry it as far as a patient's lungs. The problem is obviously more acute where the patient has a restricted peak flow.

Generally, inhalers of this kind have an air inlet passage leading to a dispensing chamber in which the medicament is located prior to inhalation, and an inhalation passage leading from the dispensing chamber and terminating in a nozzle which is placed in the patient's mouth prior to inhalation. The present invention relates to a number of refinements of the design of these components to produce improved penetration of the medicament into the lungs of the patient, particularly where the patient's peak flow is low.

U.S. Pat. No. 3,938,516 discloses an inhalation device having the basic layout described above. The medicament is inserted into the inhalation device in one half of a conventional medicament capsule which has been opened. The medicament lies below the flow-path for air through the device constituted by the air inlet passage and the inhalation passage and in order to promote the entraining of the medicament, an additional air passage is provided in the form of a tube extending at right angles to the main air passage and dipping into the opened capsule. Negative pressure produced by the venturi effect in the main air passage is used to draw air through this auxiliary air passage into the capsule to lift the medicament up into the main air-stream. This design lacks versatility in that it cannot readily be adapted for operation in conjunction with a multiple dose dispensing mechanism and is heavily reliant upon sufficient flow rate being generated in the main air passage to produce the necessary negative pressure to draw air in through the auxiliary air passage.

The present invention provides in a first aspect a dry powder inhaler comprising a dispensing chamber for receiving a charge of powder to be dispensed, said chamber having a floor upon which said charge lies prior to inhalation, an air inlet passage having at its outlet end a nozzle protruding into said dispensing chamber directed towards said floor thereof and an inhalation passage exiting from said chamber through which said powder may be inhaled entrained in air drawn into the inhaler through said air inlet passage, wherein said air inlet passage terminating in said nozzle is the principal or sole route for air to enter said dispensing chamber in use.

Preferably, the nozzle of the air inlet passage at its outlet end is directed transversely with respect to the exit of the inhalation passage from the dispensing chamber as well as being directed toward the floor of the dispensing chamber. This configuration of the direction of the nozzle at the outlet end of the air inlet passage provides maximum turbulence to lift the powder off the floor of the dispensing chamber and into the air-flow and to separate where appropriate the fine medicament particles from the larger carrier particles.

It should be understood that the "floor" of the dispensing chamber upon which the powder lies before inhalation may be provided at the base of the dispensing chamber or at an elevated position within the dispensing chamber on top of some form of platform.

The nozzle preferably extends to within 1 to 3 mm of the floor of the dispensing chamber, e.g. approximately 2 mm, measured in the direction of the air-flow exiting from the nozzle.

In a second aspect the invention includes a dry powder inhaler comprising a dispensing chamber for receiving a charge of powder to be dispensed, an inlet passage having its outlet end at said chamber, and an inhalation passage having an inlet at said chamber and an outlet through which the powder may be inhaled, wherein said inhalation passage comprises first and second portions, the first portion being upstream of the second portion and having a roof and a floor both of which rise progressively with respect to a straight line drawn from the centre of said inlet to the centre of said outlet and the second portion having a roof and a floor both of which fall progressively with respect to said line in the downstream direction.

Preferably, the first portion of the inhalation passage at its upstream end and the second portion of the inhalation passage at its downstream end extend at an angle to one another of 6 to 12°, e.g. approximately 9°. Preferably, the inhalation passage terminates at a mouthpiece defining an axis which will generally be horizontal in use and said first portion of said inhalation passage extends at an angle of from 5 to 9° upwardly with respect to said axis. Preferably, the second portion of the inhalation passage terminates extending at an angle downwardly of from 1 to 3° with respect to said axis. A preferred value for the angle of the first portion with respect to the axis is about 7° and for the second portion of the inhalation passage a preferred angle is approximately 2°.

It has been found that by angling the first and second portions of the inhalation passage in this way, the carry of medicament particles into the lungs of a patient is improved in comparison to use of a conventional straight horizontal inhalation passage.

In a third aspect the invention includes a fine powder inhaler comprising a dispensing chamber for receiving a charge of powder to be dispensed, said chamber having a floor upon which said charge lies prior to inhalation, a curved air inlet passage having an inlet end at or adjacent a wall of the inhaler and its outlet end at said dispensing chamber, and an inhalation passage extending from said dispensing chamber through which said powder may be inhaled, wherein the air inlet passage runs initially in substantially the same direction as the exit of the inhalation passage from the dispensing chamber and curves around such that the outlet end of the air inlet passage is directed laterally in said dispensing chamber and transverse to said inhalation passage as it exits the dispensing chamber. This arrangement of the air inlet passage has been found to improve the flow through the dispenser by reducing the pressure drop and producing good turbulence in the dispensing chamber. The air inlet passage is preferably horn shaped.

A single embodiment of the invention preferably incorporates all of the preferred features of the first, second and third aspects of the invention.

According to any aspect of the invention, the inhaler preferably further includes a reservoir for powder to be dispensed and user-operable mechanism for repeatedly discharging a single dose of said powder from said reservoir into said dispensing chamber as a charge of powder for inhalation.

We have found that when the quantity of powder obtained in each dose from a multidose dry powder inhaler is measured, significant variations may be detected which we ascribe to variations in the packing density of the powder in the reservoir of the device caused by the movement of the powder within the reservoir as the inhaler is carried or manipulated. Accordingly, in a fourth aspect, the invention provides a dry powder inhaler comprising a reservoir containing multiple doses of dry powder to be inhaled from said inhaler and having an outlet at a lower end thereof through which said dry powder is fed dosewise by gravity, wherein the reservoir contains a shield member supported by said dry powder so as to fall progressively as said powder is fed from said reservoir in use.

The invention will be further illustrated by the following description of a preferred embodiment with reference to the accompanying drawings in which.

Figure 4:
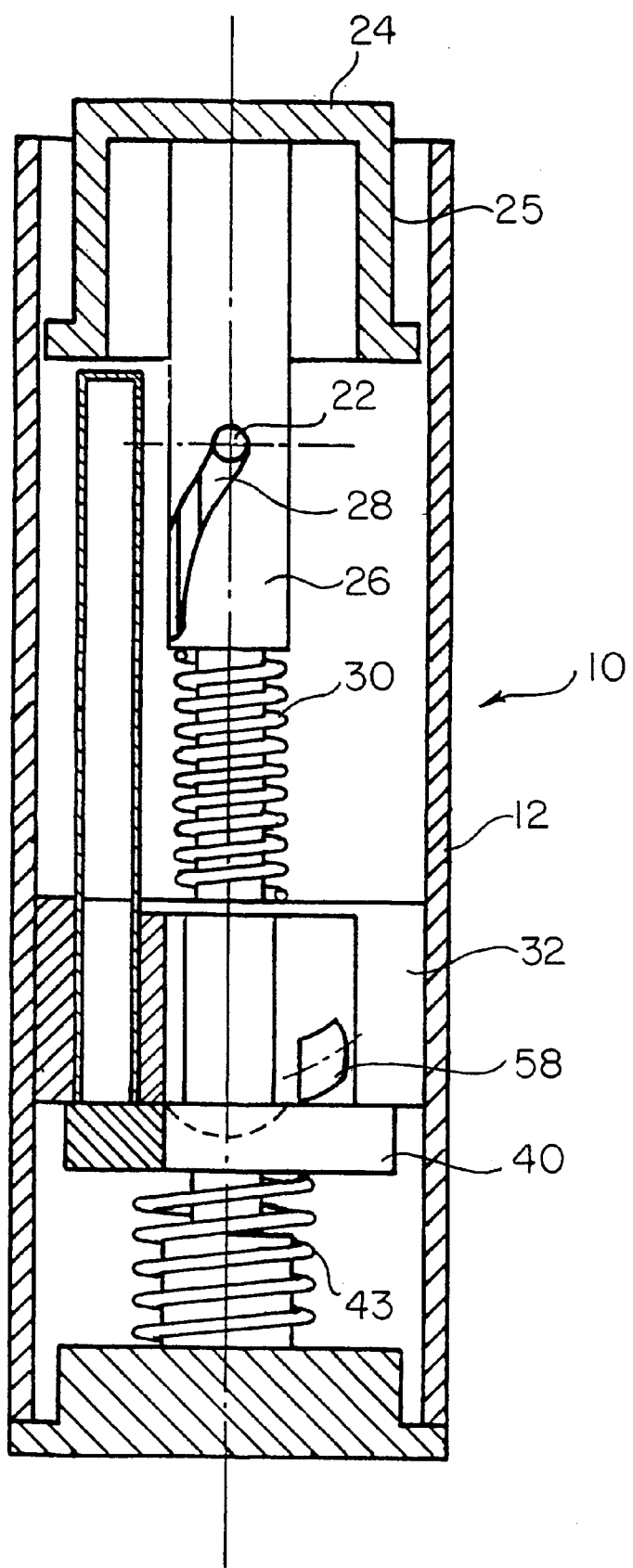
FIG. 4 is a vertical cross-section of the inhaler of FIG. 1 on the stepped section line IV—IV in FIG. 2.
Figure 5:
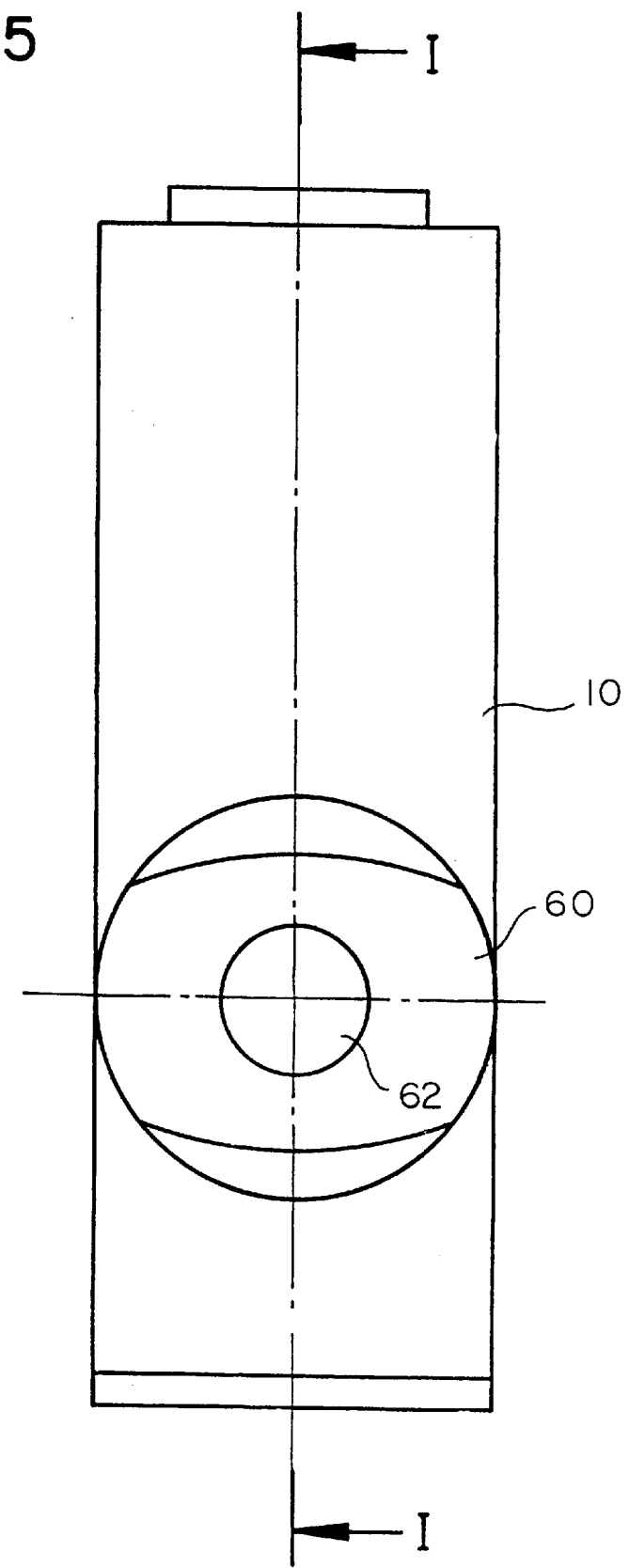
FIG. 5 is a front view of the inhaler of FIG. 1.

As shown in the accompanying drawings, an inhaler according to the present invention in all three of its aspects is provided which comprises a casing 10 having a tubular side wall 12 which in cross-section has the form of a circle truncated by two parallel diametrically opposed chords. The casing is closed at its lower end by a plug 14 and has a pair of diametrically opposed circular through apertures 16 in the curved parts of its side wall 12, each of approximately 10 mm diameter. A circular cross-section post 18 rises from a recess in an upstanding boss 20 on the upper surface of the plug 14 axially within the wall 12. A cross-pin 22 extends diametrically through the upper end of the post 18 and projects out from either side. A cap 24 is received within the upper end of the wall 12 and has a circum-ambient side wall 25 and a long downwardly extending hollow cylindrical boss 26 extending over the upper end of the rod 22. The boss is provided with a pair of diametrically opposed helical slots 28 (FIG. 4) receiving the projecting ends of the pin 22. A coil compression spring 30 is positioned over the post 18 below the boss 26 of the cap 24 to spring bias the cap upwardly. At its lower end, the coil spring 30 is supported on the upper surface of a block 32 extending diametrically across the bore of the casing side wall 12.

A pair of arcuate cross-section plates 34, 36 extend as shields down from front and rear bottom edges of the cap side wall 25, as a sliding fit within the curved wall portions of the casing side wall 12. Part circular slots 38 are provided between the inside of the bottom of the casing side wall 12 and a main part of the plug 14 received within the casing side wall. Circular apertures 16' are provided in the shield plates 34, 36. When the cap 24 is fully depressed, the apertures 16' align with the apertures 16, to which they correspond also in size.

Figure 1:
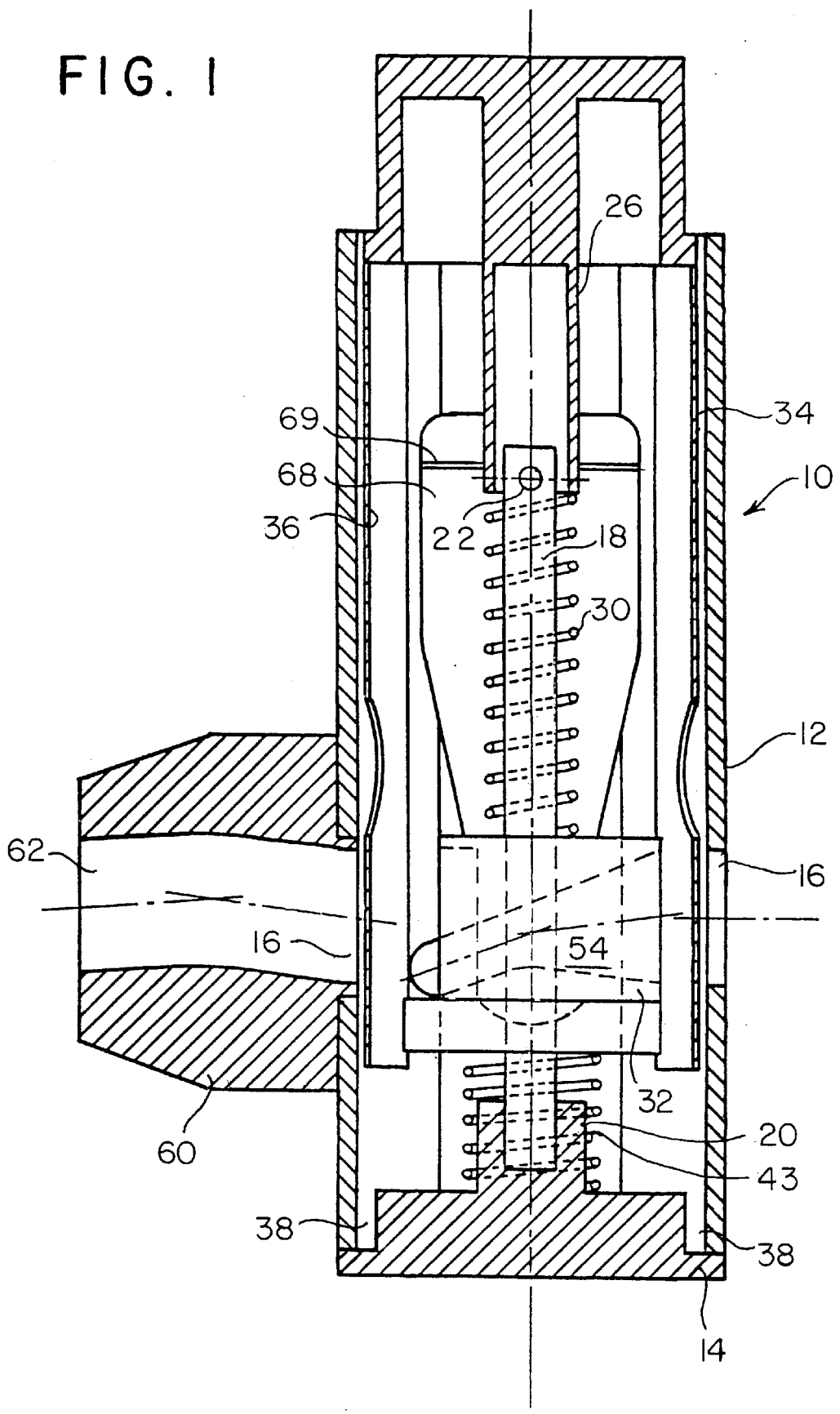
FIG. 1 is a cross-sectional elevation view of an inhaler according to all three aspects of the invention taken on the line I—I of FIG. 5 with the inhaler cap in its up position.
Figure 2:
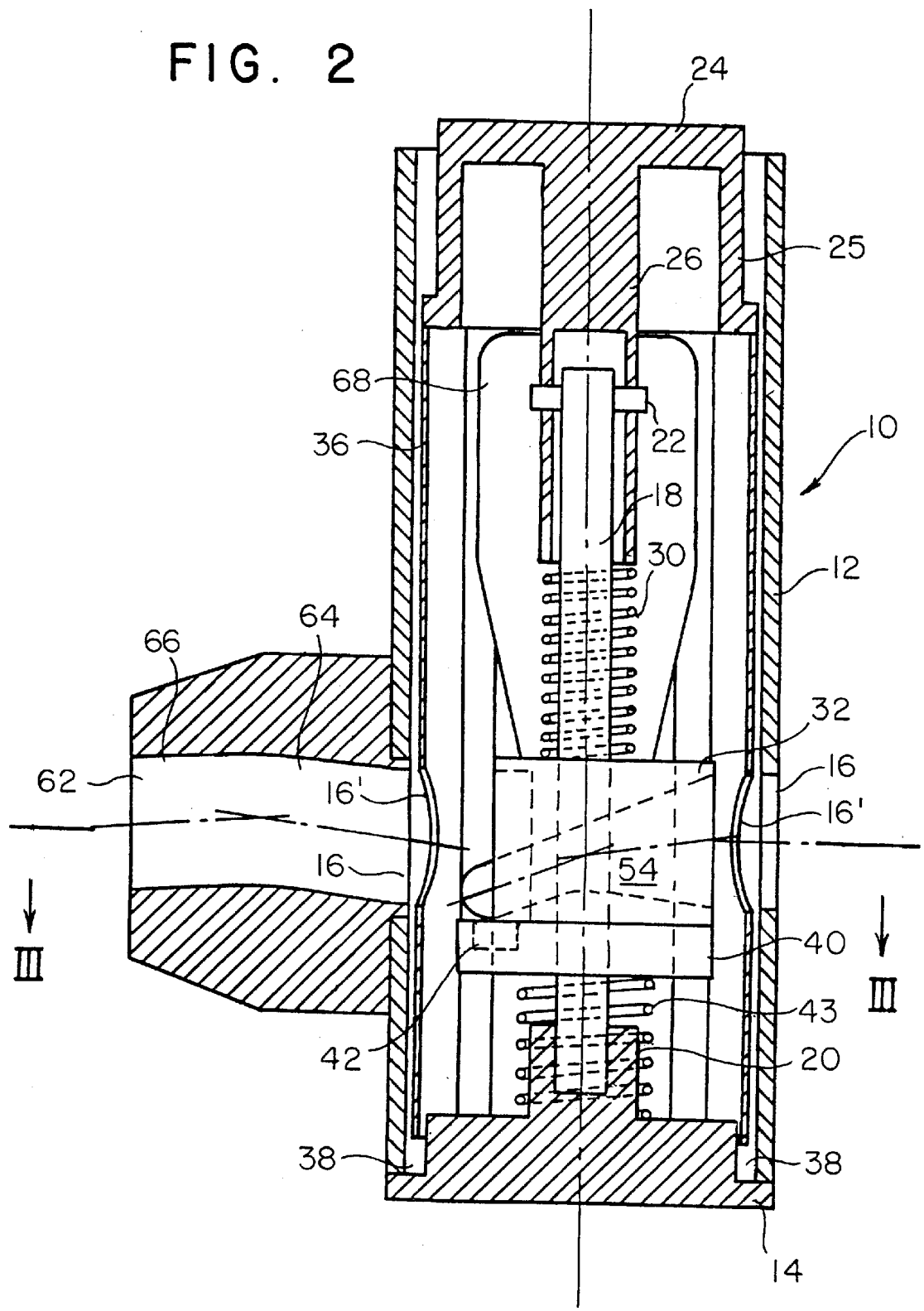
FIG. 2 is a view similar to FIG. 1, but with the inhaler cap depressed.

As below the plug 32 on the post 18 is a disc 40 having in its upper surface a recess 42. Disc 40 is fixed with respect to rotation to the post 18 and turns through 90° with the post 18 in response to downward movement of the cap 24 forcing the pin 22 to track the helical slot 28. Axially, the disc 40 is supported by a coil compression spring 43 which extends down over the boss 20 to the upper surface of the plug 14. The height of the upper surface of disc 40 is preferably at or slightly above the lowest part of the bore of the inhalation passage 62 described below. Hence, the surface of disc 40 is preferably slightly higher than is shown in FIG. 1, so that there is no step upwards in going to the inhalation passage.

Figure 7:
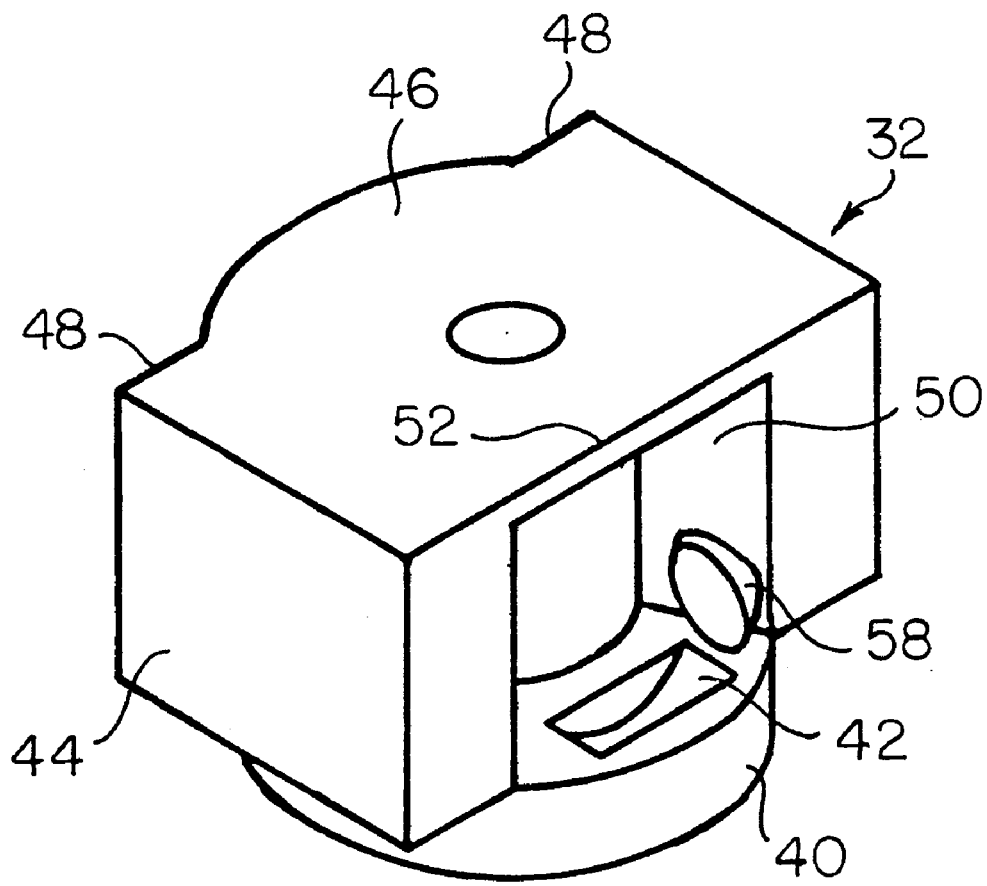
FIG. 7 is a perspective view of the block 32 shown in FIG. 3 and the underlying disc.

As shown in FIG. 7 the block 32 is generally rectangular having a pair of shorter opposed end faces 44 which abut the flat side portions of the casing wall 12. One longer side face of the block 32 faces the rear of the inhaler and has a vertically running part cylindrical protrusion 46 extending over a central region thereof flanked by flat wall portions 48. The opposite side wall of the block 32 has a cavity 50 in the centre thereof which has no floor but has a roof 52. A floor for the cavity is provided by the underlying disc 40.

The cavity 50, together with the disc 40, thus define a dispensing chamber.

Figure 6:
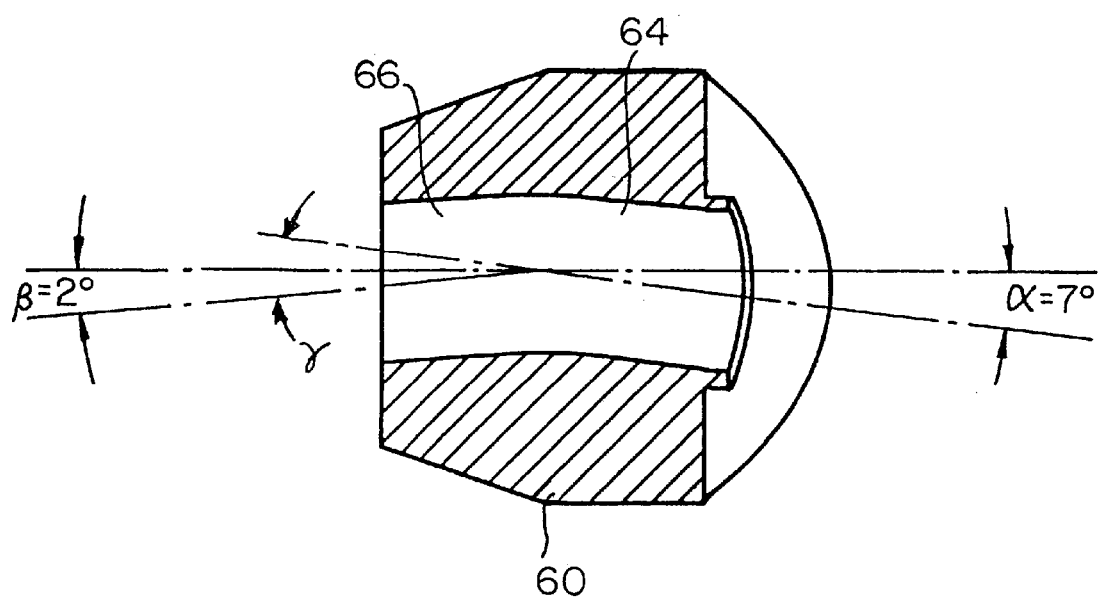
FIG. 6 is an illustration of the angles of the first and second portions of the inhalation passage of the inhaler shown in FIG. 1.

The block 32 contains or defines a horn-shaped tubular air inlet passage 54 which extends from an inlet aperture 56 on the rear of the block in the centre of protrusion 46 and curves around and narrows to reach a nozzle 58 which protrudes from the side wall of the cavity 50. The nozzle 58 points laterally and downwardly into the dispensing chamber. Extending from the front aperture 16' of the casing 10 is a mouthpiece 60 having an inhalation passage 62 of 10 mm diameter extending therethrough which is divided into a first, upstream portion 64 and a second, downstream portion 66. The mouthpiece 60 is for insertion into the mouth of a patient in a generally horizontal attitude. The first portion 64 of the inhalation passage is cylindrical and has parallel upper and lower wall surfaces which extend upwardly with respect to an axial line through the mouthpiece connecting the centres of the upstream and downstream ends of the inhalation passage 62. The second portion of the inhalation passage 66 is also cylindrical but extends at a downwards angle to the said axis from the downstream end of the first portion 64 to the outlet of the mouthpiece. As shown in FIG. 6, the roof of the first upstream portion 64 makes an angle α to the axis of the mouthpiece and the horizontal of about 7° whilst the second portion 66 makes an angle β to the axis (the horizontal) of approximately 2° downwards so that the angle between the two passageway portions is about 9° (γ).

A reservoir 68 for medicament lies to one side of the post 18 and has a downwardly facing discharge opening closed by disc 40. A shield member 69 floats on the top of the powder medicament and falls as the medicament level falls. In the position of disc 40 corresponding to the cap 24 being fully raised by the spring 30, the recess 42 lies beneath the discharge opening of the reservoir 68.

Figure 3:
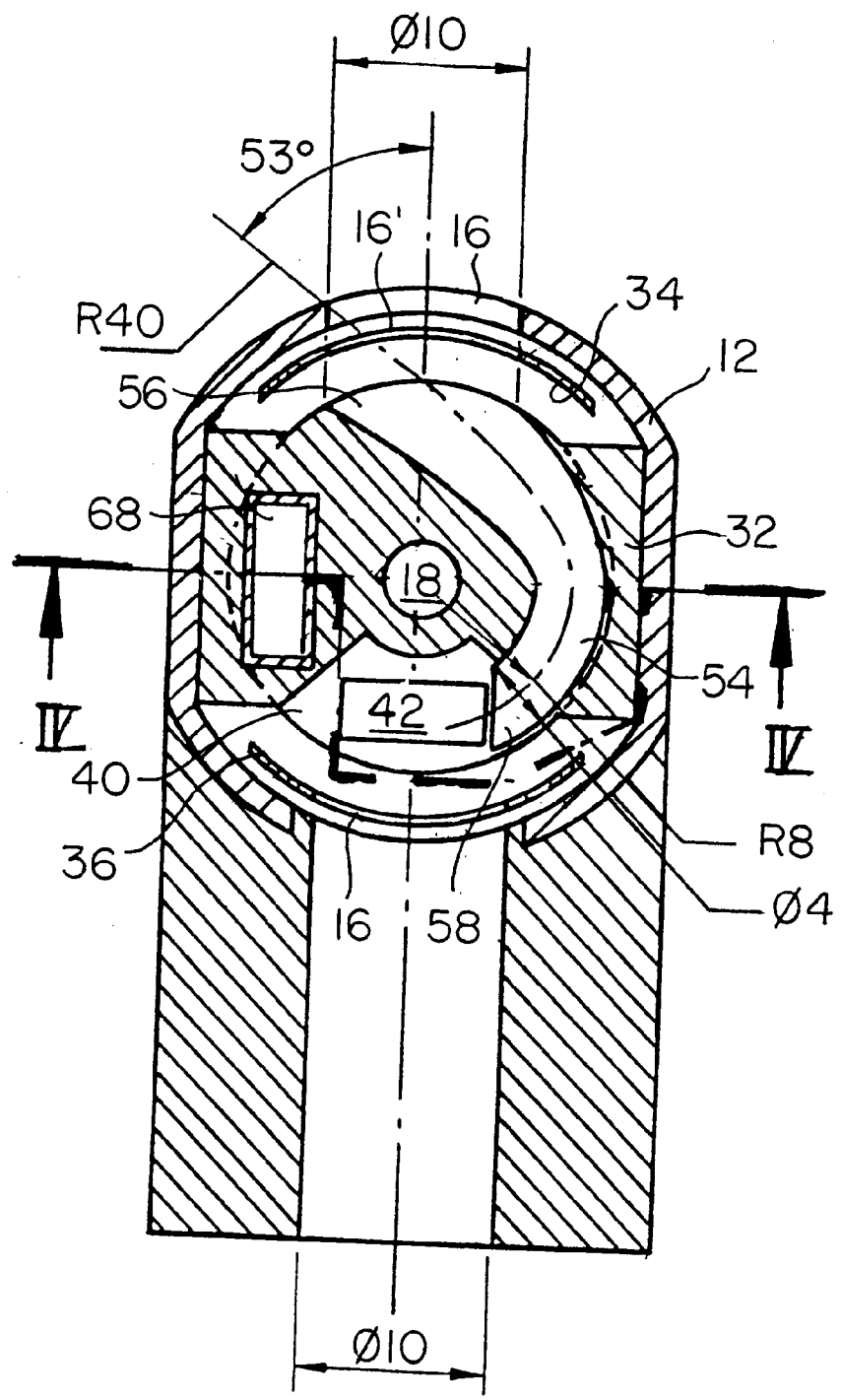
FIG. 3 is a horizontal cross-section of the inhaler shown in FIG. 1 taken on the line III—III marked in FIG. 2.

The horn-shaped air inlet passage 54 has its circular opening 56 of 10 mm diameter centrally positioned on the protrusion 46 of the block 32 facing the aperture 16 in the rear of casing wall 12. The passage 54 curves around the post 18 and narrows progressively to have a diameter of 4 mm where it exits from the side wall of the cavity 50 at the start of the nozzle 58. The curvature of the passage is such that the outer wall surface has a radius of curvature of 40 mm where marked R40 in FIG. 3 and a radius of curvature of 8 mm where marked R8 in FIG. 3.

To use the dispenser, the user first presses the cap down fully and holds it depressed. The disc 40 is rotated through 90° to bring the recess 42 into the floor area of the dispensing chamber carrying a dose of medicament from the reservoir 68.

When a user places the mouth piece 60 into the user's mouth and inhales, a blast of air is drawn in through the inlet 16 to enter the dispensing chamber as a jet through the nozzle in a direction which is both downwardly onto the medicament and laterally across the dispensing chamber with respect to the mouthpiece. This causes high turbulence producing good separation of fine drug particles from coarse carrier particles when the medicament is of that type and causing good entraining of the medicament particles into the air-stream.

The angling of the portions of the inhalation passage provides good penetration of the entrained powder into the patient's lungs.

To demonstrate this, salbutamol sulphate/lactose particles were "inhaled" from an inhaler as shown in the drawings using a test apparatus in which a series of glass vessels is used to simulate the airway and lungs of a patient. A modified version of the inhaler having a straight inhaler passage was tested as a basis for comparison. Deposition in the "first stage" of the apparatus is intended to simulate deposition in the mouth of a patient. The results are shown in the Table. It can be seen that less medicament is expected to be lost in the patient's mouth using the angled inhalation passage.

TABLE

|  | Straight Inhalation passage | Angled Inhalation passage |
|---|---|---|
| % of powder trapped in first stage | 45.8 | 33.6 |

Whilst the invention has been described with reference to the illustrated embodiment and its particular characteristics, many variations and modifications thereof are possible within the scope of the invention.

We claim:

1. A dry powder inhaler comprising a dispensing chamber for receiving a charge of powder to be dispensed, said chamber having a floor, an air passage having an inlet end and an outlet end and its outlet end terminating at a nozzle directed downwardly into said dispensing chamber whereby air is directed across and toward said floor thereof to discharge said charge of powder from said dispensing chamber and an inhalation passage exiting from said chamber and wherein said air inlet passage is at least the principal route for air to enter said dispensing chamber during use.

2. An inhaler as claimed in claim 1, wherein the nozzle of the air inlet passage at its outlet end is directed transversely with respect to the exit of the inhalation passage from the dispensing chamber as well as being directed toward the floor of the dispensing chamber.

3. An inhaler as claimed in claim 1, wherein said nozzle extends to within from 1 to 3 mm of the floor of the dispensing chamber.

4. An inhaler as claimed in claim 1 wherein the air inlet passage runs initially in substantially the same direction as the exit of the inhalation passage from the dispensing chamber and curves around such that the outlet end of said air inlet passage is directed laterally in said dispensing chamber and transverse to said inhalation passage as it exits the dispensing chamber.

5. An inhaler as claimed in claim 1, further including a reservoir for powder to be dispensed and a user operable mechanism for repeatedly discharging a single dose of said powder from said reservoir as a charge of powder for inhalation.

6. An inhaler as claimed in claim 1, wherein said dispensing chamber is recessed.

7. A dry powder inhaler comprising a dispensing chamber for receiving a charge of powder to be dispensed, an air inlet passage having its outlet end at said chamber, and an inhalation passage having an inlet at said chamber and an outlet, wherein said inhalation passage comprises first and second portions each having a respective longitudinal axis, the first portion being upstream of the second portion and having a roof and a floor both of which rise progressively with respect to a straight line drawn from the center of said inhalation passage inlet to the center of said inhalation passage outlet and the second portion having a roof and a floor both of which fall progressively with respect to said line in the downstream direction, such that said first portion of the inhalation passage at its downstream end and the second portion of the inhalation passage at its upstream end meet and their respective longitudinal axes extend at an angle to one another of from 6 to 12°.

8. An inhaler as claimed in claim 7, wherein said chamber has a floor, and said air inlet passage has at its outlet end a nozzle protruding into said dispensing chamber directed toward said floor thereof.

9. An inhaler as claimed in claim 8, wherein said nozzle is directed transversely to the direction of exit of the inhalation passage from the dispensing chamber as well as being directed toward the floor of the dispensing chamber.

10. An inhaler as claimed in claim 7, wherein the air inlet passage is at least the principal route for air to enter the dispensing chamber in use.

11. An inhaler as claimed in claim 7, wherein the air inlet passage runs initially in substantially the same direction as that in which the inhalation passage exits from the dispensing chamber and curves around such that the outlet end of said air inlet passage is directed laterally in said dispensing chamber and transverse to said inhalation passage as it exits the dispensing chamber.

12. An inhaler as claimed in claim 7, further including a reservoir for powder to be dispensed and a user operable mechanism for repeatedly discharging a single dose of said powder from said reservoir as a charge of powder for inhalation.

13. A dry powder inhaler comprising a dispensing chamber for receiving a charge of powder to be dispensed, said chamber having a floor, a curved air inlet passage having an inlet end at or adjacent a wall of the dispenser and an outlet end at said dispensing chamber, and an inhalation passage extending from said dispensing chamber, wherein the air inlet passage runs initially in substantially the same direction as that in which the inhalation passage exits from the dispensing chamber and curves around such that the outlet end of said air inlet passage is directed laterally and downwardly into said dispensing chamber and transverse to said inhalation passage as it exits from the dispensing chamber.

14. An inhaler as claimed in claim 13, further including a reservoir for powder to be dispensed and a user operable mechanism for repeatedly discharging a single dose of said powder from said reservoir as a charge of powder for inhalation.

15. An inhaler as claimed in claim 13, wherein said dispensing chamber is recessed.

* * * * *